United States Patent
Lin et al.

(10) Patent No.: US 9,823,318 B2
(45) Date of Patent: Nov. 21, 2017

(54) METHOD FOR CORRELATING MAGNETIC RESONANCE IMAGES WITH HISTOLOGICAL SECTIONS

(71) Applicant: Chang Gung Memorial Hospital, Linkou, Gueishan Township, Taoyuan County (TW)

(72) Inventors: Yu-Chun Lin, Gueishan Township, Taoyuan County (TW); Jiun-Jie Wang, Gueishan Township, Taoyuan County (TW); Chun-Chieh Wang, Gueishan Township, Taoyuan County (TW); Yi-Ping Lin, Gueishan Township, Taoyuan County (TW); Gigin Lin, Gueishan Township, Taoyuan County (TW)

(73) Assignee: Chang Gung Memorial Hospital, Linkou, Gueishan Township, Taoyuan County (TW)

( * ) Notice: Subject to any disclaimer, the term of this patent is extended or adjusted under 35 U.S.C. 154(b) by 561 days.

(21) Appl. No.: 14/595,602

(22) Filed: Jan. 13, 2015

(65) Prior Publication Data
US 2016/0018488 A1    Jan. 21, 2016

(30) Foreign Application Priority Data

Jul. 15, 2014 (TW) .............................. 103124256 A

(51) Int. Cl.
| | |
|---|---|
| *G01V 3/00* | (2006.01) |
| *G01R 33/31* | (2006.01) |
| *G01R 33/30* | (2006.01) |
| *A61B 5/055* | (2006.01) |
| *G01N 1/06* | (2006.01) |
| *G01N 1/31* | (2006.01) |

(Continued)

(52) U.S. Cl.
CPC .............. *G01R 33/30* (2013.01); *A61B 5/055* (2013.01); *G01N 1/06* (2013.01); *G01N 1/31* (2013.01); *G01N 1/36* (2013.01); *G01N 1/42* (2013.01); *A61B 2503/40* (2013.01)

(58) Field of Classification Search
CPC ..... G01R 33/30; A61B 5/055; A61B 2503/40; G01N 1/06; G01N 1/31; G01N 1/36; G01N 1/42
USPC ......................................................... 324/309
See application file for complete search history.

(56) References Cited

U.S. PATENT DOCUMENTS 4,752,347 A * 6/1988 Rada ........................ G01N 1/36
156/382
6,873,156 B2 * 3/2005 Ferris ................... A61B 5/0555
324/309

(Continued)

*Primary Examiner* — Susan Lee
(74) *Attorney, Agent, or Firm* — Panitch Schwarze Belisario & Nadel LLP

(57) ABSTRACT

In a method for correlating magnetic resonance images with histological sections, a target tissue of a living animal is embedded in an enclosed matrix of an optical cutting temperature compound to obtain a packaged specimen on a platform oriented in a first guiding plane. The packaged specimen on the platform is subjected to an MRI examination by scanning along imaging planes parallel to the first guiding plane, and then subjected to a frozen sectioning procedure along sectioning planes in parallel with a second guiding plane which is parallel to the first guiding plane.

5 Claims, 7 Drawing Sheets

(51) Int. Cl.
*G01N 1/36* (2006.01)
*G01N 1/42* (2006.01)

(56) References Cited

U.S. PATENT DOCUMENTS

| | | | | |
|---|---|---|---|---|
| 8,041,409 B2* | 10/2011 | Leevy | ................... | A61B 5/0059 |
| | | | | 250/336.1 |
| 8,482,278 B2* | 7/2013 | Wolke | ..................... | G01R 33/30 |
| | | | | 324/309 |
| 2001/0053878 A1* | 12/2001 | Ferris | ................... | A61B 5/0555 |
| | | | | 600/415 |
| 2014/0031669 A1* | 1/2014 | Hensley | ............... | A61B 5/0071 |
| | | | | 600/411 |
| 2014/0107523 A1* | 4/2014 | Petraglia | ................... | A61D 3/00 |
| | | | | 600/553 |

* cited by examiner

METHOD FOR CORRELATING MAGNETIC RESONANCE IMAGES WITH HISTOLOGICAL SECTIONS

CROSS-REFERENCE TO RELATED APPLICATION

This application claims priority from Taiwanese application no. 103124256, filed on Jul. 15, 2014, the disclosure of which is incorporated in its entirety herein by reference.

FIELD OF THE INVENTION

This invention relates to a method for correlating magnetic resonance images with histological sections.

BACKGROUND OF THE INVENTION

Magnetic resonance imaging (MRI), a non-invasive technique, is extensively used in biomedical research.

Diffusion MRI is a technique that is used to measure water mobility within tissues. The diffusion pattern of water molecules in tissues reflects tissue microstructure, such as tumor response to treatment. Diffusion MR images (i.e., diffusion weighted (DW) images) are typically acquired by single-shot echo-planar imaging (EPI) sequences, which are susceptible to inhomogeneity of the magnetic field ($B_0$ field), resulting in signal loss and geometric distortion. Several methods were developed to cope with susceptibility artifacts, such as gradient compensation, advanced shimming techniques, modified pulse sequences, and post processing corrections. However, most of the proposed methods require dedicated MR pulse sequence editors or sophisticated calibration algorithms, which are not readily available for commercial scanners. Alternatively, Fluorinert™, a proton free perfluorinated electronic liquid, has been proposed to effectively reduce susceptibility artifacts by homogenizing the $B_0$ field around the target tissue.

The biological meaning of the acquired images (DW images) has to be analyzed by a thorough histological examination. Thus, after acquiring the DW images, the target tissue need be embedded in an embedding medium, such as an optimal cutting temperature (OCT) compound, for cryostat sectioning (frozen sectioning).

However, it is difficult to correlate histological sections obtained by a frozen sectioning procedure with the DW images because of the distortion of the DW images and differences in section angle and thickness.

Furthermore, if the target tissue is embedded in the Fluorinert™ electronic liquid for a diffusion MRI examination, it need be removed from the Fluorinert™ electronic liquid and then embedded in another embedding medium for cryostat sectioning.

SUMMARY OF THE INVENTION

Therefore, an object of the present invention is to provide a method for correlating magnetic resonance images with histological sections. In the present invention, a target tissue of a living animal is embedded in an optimal cutting temperature (OCT) compound for an MRI examination, and the target tissue embedded in the OCT compound can be subsequently sectioned directly for histological examination in an orientation matching that of the imaging planes for the MRI examination.

According to the present invention, there is provided a method for correlating magnetic resonance images with histological sections. The method includes the steps of:

(a) embedding a target tissue of a living animal in an enclosed matrix of an optimal cutting temperature compound to obtain a packaged specimen which is disposed on a platform such that the packaged specimen is oriented in a first guiding plane;

(b) subjecting the packaged specimen on the platform to an MRI examination by scanning the packaged specimen along imaging planes oriented parallel to the first guiding plane, thereby obtaining magnetic resonance images of the packaged specimen;

(c) transferring the packaged specimen to a cryostat; and (d) subjecting the packaged specimen in the cryostat to a frozen sectioning procedure along sectioning planes in parallel with a second guiding plane which is parallel to the first guiding plane, to thereby obtain histological sections each of which is readily correlatable with a corresponding one of the magnetic resonance images.

BRIEF DESCRIPTION OF THE DRAWINGS

Other features and advantages of the present invention will become apparent in the following detailed description of the embodiment of the invention, with reference to the accompanying drawings, in which.

DETAILED DESCRIPTION OF THE EMBODIMENT

A method for correlating magnetic resonance images with histological sections according to an embodiment of this invention includes steps (a) to (d).

Figure 1:
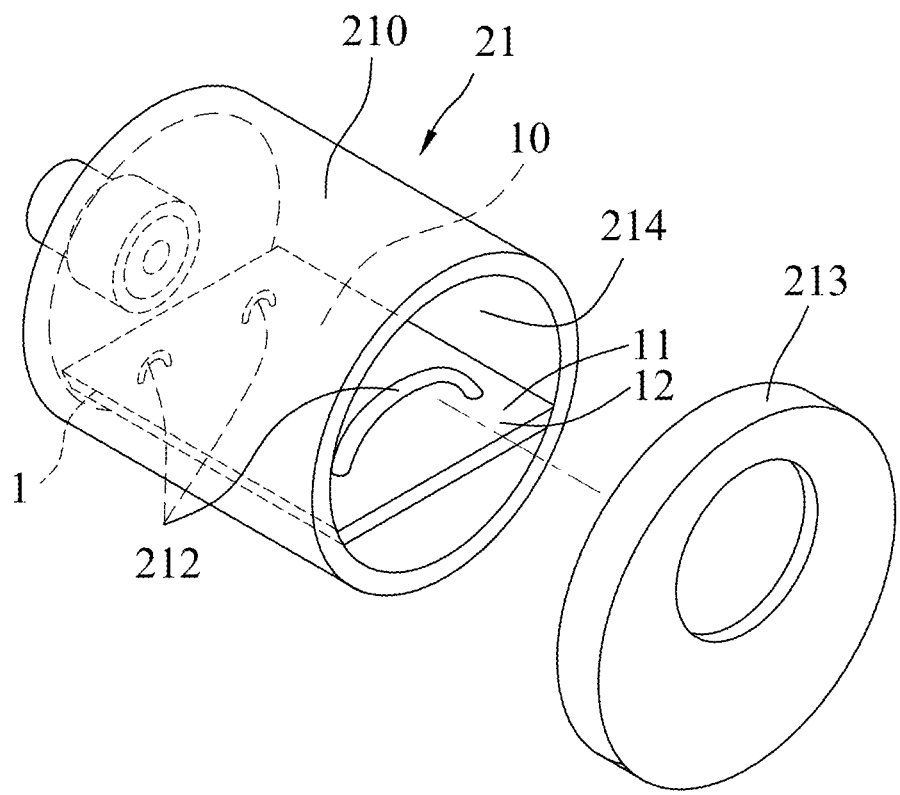
FIG. 1 is a schematic view of a platform which is disposed in a container and which is used in a method for correlating magnetic resonance images with histological sections according to an embodiment of this invention.
Figure 2:
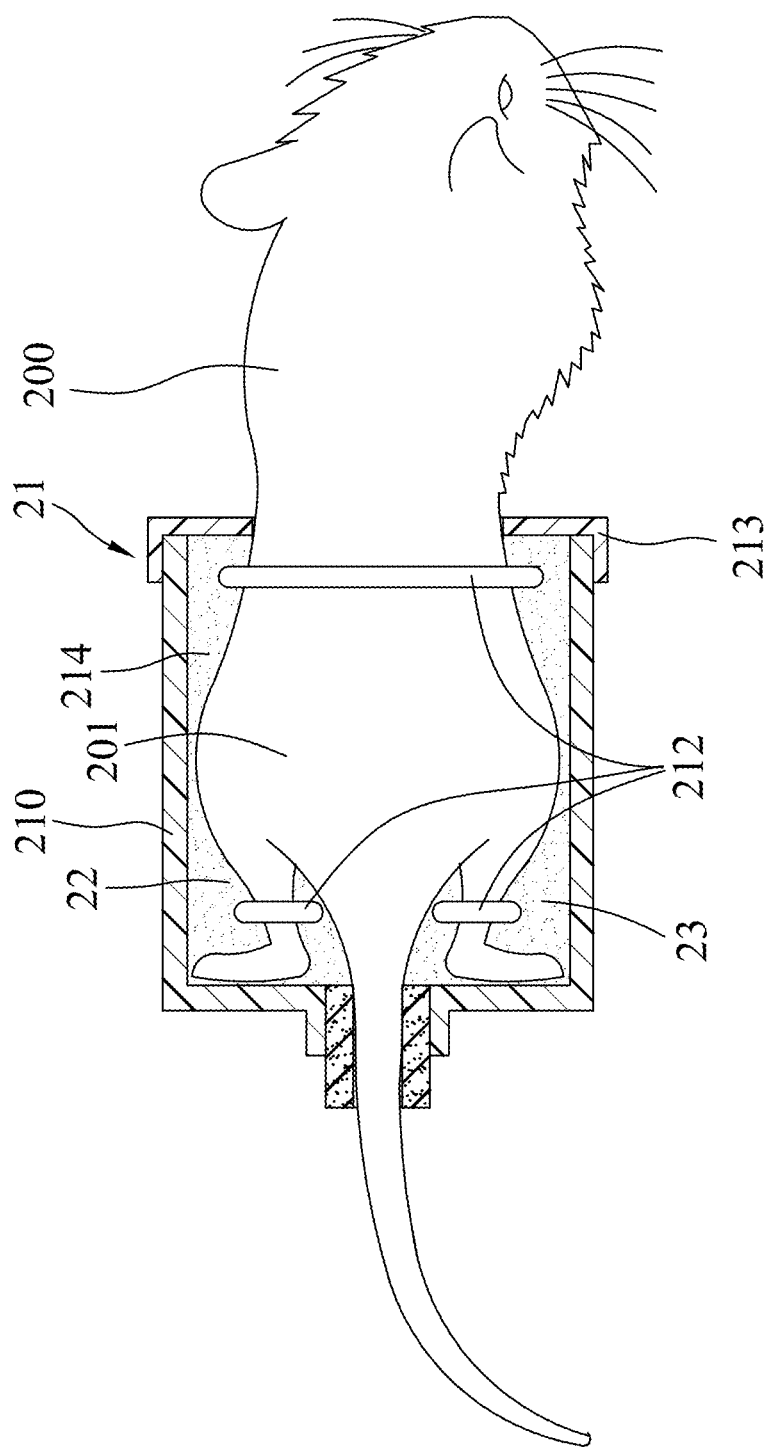
FIG. 2 is a partially sectioned view showing a target tissue of a mouse embedded in the container of FIG. 1.

With reference to FIG. 2, in step (a), a target tissue 201 of a living animal 200 is embedded in an enclosed matrix 22 of an optimal cutting temperature (OCT) compound to obtain a packaged specimen 23, which is disposed on a platform 1 (see FIG. 1) such that the packaged specimen 23 is oriented in a first guiding plane 11. The OCT compound is commercially available, and is a water-soluble transparent polymeric liquid including glycols and resins. The OCT compound is in gel state at room temperature, and in solid state at a temperature lower than −10° C.

In step (b), the packaged specimen 23 is subjected to an MRI examination by scanning along imaging planes oriented parallel to the first guiding plane 11, thereby obtaining magnetic resonance images of the packaged specimen 23.

Step (c) includes a substep (c1) of transferring the packaged specimen 23 to a cryostat (not shown).

In step (d), the packaged specimen 23 in the cryostat is subjected to a frozen sectioning procedure along sectioning planes in parallel with a second guiding plane 12 (see FIG. 1) which is parallel to the first guiding plane 11 to thereby obtain histological sections, each of which is readily correlatable with a corresponding one of the magnetic resonance images.

In this embodiment, the living animal 200 is a mouse, and the target tissue 201 is located at a lower half of the mouse 200. In step (a), the lower half of the mouse 200 is fixed to a flat surface 10 of the platform 1 using three fixing members 212. Then the platform 1 is disposed in a container 21. The container 21 includes a main body 210 and a top cover 213. The platform 1 is disposed in the main body 210 such that the tail of the mouse 200 extends through a bottom hole in the main body 210 and an upper half of the mouse 200 extends outwardly of a top opening of the main body 210. Next, the bottom hole is sealed and the OCT compound is poured into the main body 210 from the top opening to fill the main body 210. The top opening is subsequently sealed by the top cover 213. Thus, the enclosed matrix 22 of the OCT compound is disposed in an enclosed space 214 defined between the container 21 and the platform 1. The flat surface 10 of the platform 1 extends in an in-plane direction and defines both the first and second guiding planes 11, 12, i.e., the flat surface 10 has both the first and second guiding planes 11, 12.

In addition, the lower half of the mouse 200 is shaved to prevent air bubbles formed between the mouse 200 and the OCT compound. Because the OCT compound has an osmotic pressure similar to that of the cells of the mouse 200, when the target tissue is rapidly cooled to a very low temperature (−70° C.), defects (wrinkles, breakage, etc.) formed during the frozen sectioning procedure may be reduced.

The container 21 can be formed by any suitable process, for example, punching molding, injection molding, or three dimensional printing.

In step (b) of this embodiment, the packaged specimen 23 is subjected to a diffusion MRI examination to obtain diffusion weighted (DW) images, and the body temperature of the mouse 200 is maintained at 35-37° C.

In this embodiment, step (c), which is performed before step (d), further includes a substep (c2) of removing the platform 1 together with the packaged specimen 23 disposed thereon from the container 21 along the in-plane direction of the platform 1.

The present invention will now be explained in more detail below by way of the following experiments.

In the following, MRI experiments were performed using a 7-Tesla animal MR scanner (ClinScan, Bruker, Ettlingen, Germany) equipped with a 630 mT/m gradient coil with a slew rate of 6300 T/m/s. The regions of the 3D shimming volume were carefully adjusted to fit the regions to be imaged for all the experiments.

Phantom Experiments

A 1.5 cm cubic phantom made of 1.2% agarose gel was examined to analyze the effect of field inhomogeneity on MR imaging. To mimic areas with susceptibility differences, a fixed air bubble was introduced inside the gel. The MR images of the phantom were acquired in three conditions: (A) stand-alone, (B) embedded within a Fluorinert™ electronic liquid (3M company, MN, USA), and (C) embedded within an optical cutting temperature (OCT) compound (Tissue-Tek, Sakura Finetek, Torrance, Calif., USA).

In the above (A), (B), and (C) conditions, diffusion-weighted (DW) images were acquired using a single-shot echo planar imaging technique with repetition time (TR)= 3000 ms; echo time (TE)=35 ms; field of view (FOV)=45 mm; matrix=128×128; slice thickness=0.8 mm; and b-values=0 and 500 s/mm$^2$. Turbo spin echo (TSE) sequence T2-weighted (T2W) images (TR=3500 ms and TE=99 ms) were acquired as an anatomical reference. The $B_0$ field maps of corresponding slices were obtained using a gradient dual echo sequence with TEs=7 and 10 ms and TR=1000 ms.

Figure 3:
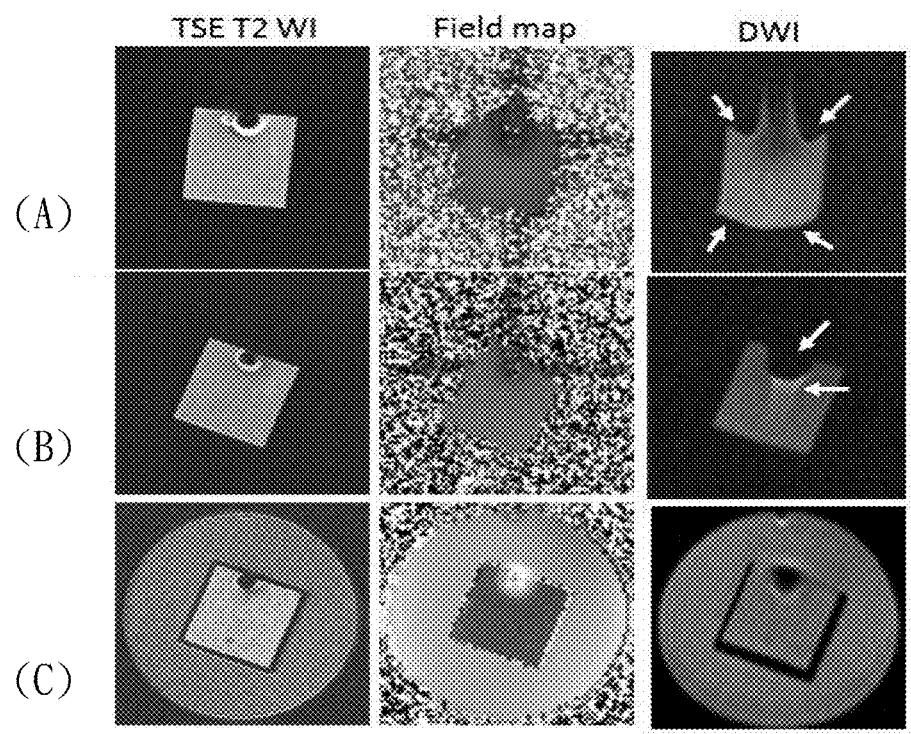
FIG. 3 shows TSE T2 weighted images, $B_0$ field maps, and DW images of a phantom in three conditions: (A) stand-alone, (B) embedded within a Fluorinert™ electronic liquid, and (C) embedded within an optical cutting temperature (OCT) compound.

FIG. 3 shows the TSE T2-weighted images, the $B_0$ field maps, and the DW images in the three conditions (A), (B), and (C). The white arrows indicate the locations of distortion artifacts in the corresponding DW images.

In condition (A), strong field differences were apparent near the air bubble and edges of the phantom, resulting in severe shape distortion in the DW image.

When the phantom was embedded in the Fluorinert™ electronic liquid (condition (B)), the shape distortion at the edge of the phantom was reduced compared with condition (A). However, the distortion and signal dropout remained prominent around the air bubble.

On the other hand, when the phantom was embedded in the OCT compound (condition (C)), a homogeneous $B_0$ field was observed, and the distortion at the edges and near the air bubble in the corresponding DW image was reduced compared with conditions (A) and (B).

Thus, it is evident that the OCT compound may reduce field inhomogeneity to correct the geometric distortion in diffusion MRI.

Animal Experiment (1) MRI Examination

Tumors were implanted into the mice (7- to 8-week-old male mice) by intramuscular inoculation of 3×10$^6$ transgenic mouse prostate adenocarcinoma (TRAMP)-C1 cells into a thigh of each mouse. On the eighth to the tenth day after tumor implantation, each mouse was anesthetized with 1-2% isoflurane in oxygen, and placed on and fixed to a platform for MRI examination. The platform served as a guide for the coronal planes (imaging planes) in the MRI examination and for the sectioning planes in the tissue sectioning examination. The mouse was subjected to the MRI examination before and after the OCT compound embedding by using the same imaging parameters. The OCT compound embedding was done by covering the lower half of the mouse in a container filled with the OCT compound (FIG. 2). In the MRI examination, the body temperature of the mouse was maintained at 35-37° C.

The imaging parameters of the DW imaging were: TR=3000 ms; TE=35 ms; FOV=45 mm; matrix=128×128; slice thickness=1 mm; b-values=0, 500, 1000, and 2000 s/mm$^2$. Transversal and coronal planes were obtained with continuous 1-mm thick slices covering the entire tumor. The DW images (coronal images) were images of slices parallel to the platform on which the mouse rested. Anatomic MR images were acquired using a T2W TSE sequence (TR=3500 ms and TE=99 ms) with the same slice orientation and geometrical parameters as the DW images.

(2) Tissue Sectioning

Each mouse was euthanized immediately after the MRI examination was finished. The target tissue of the mouse, embedded in the OCT compound, was rapidly cooled to −70° C. using liquid nitrogen, and was stored at −70° C. until sectioning. The sectioning planes of the target tissue were orientated in parallel with the platform, and corresponded to the coronal planes of the coronal MR images. The target tissue of the mouse was sectioned using a large-specimen sectioning cryomacrotome (Leica CM3600, Meyer Instruments, Houston, Tex., USA). The section thickness was 20 µm for each slice.

TSE T2-Weighted Image vs. Histological Section

Figure 4:
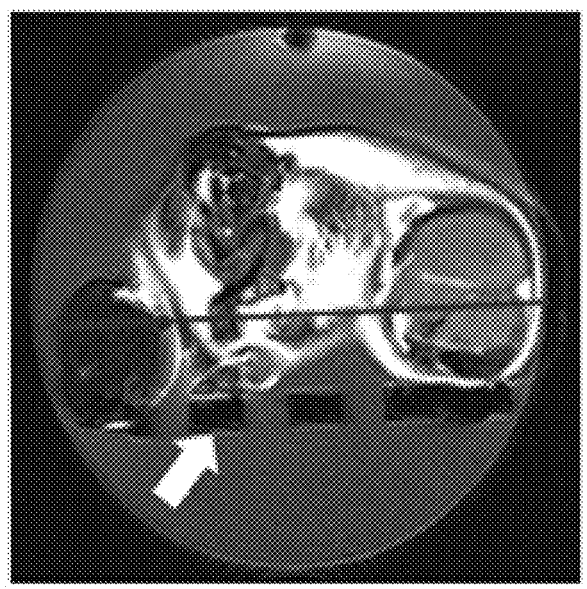
FIG. 4 is an axial TSE T2 weighted image of a mouse embedded in the OCT compound.
Figure 5:
FIG. 5 is a coronal TSE T2 weighted image of the mouse embedded in the OCT compound.
Figure 6:
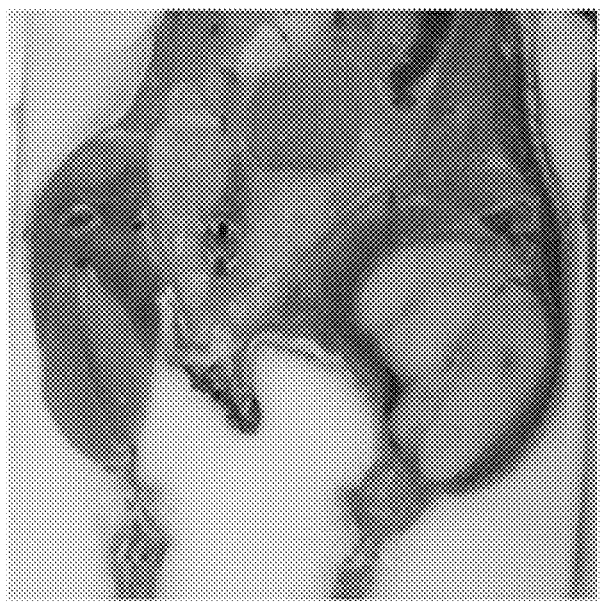
FIG. 6 shows a histological section corresponding to the coronal TSE T2 weighted image.
Figure 7:
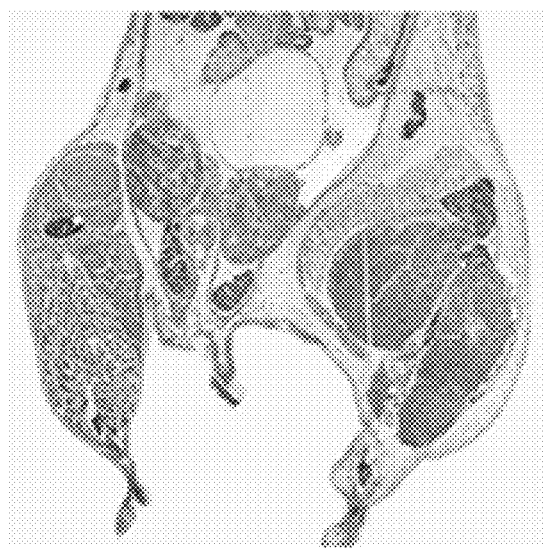
FIG. 7 shows the histological section with hematoxylin and eosin staining.

FIG. 4 shows an axial turbo spin echo (TSE) sequence T2-weighted (T2W) image (TSE T2-weighted image) of one of the mice embedded in the OCT compound. As shown, the orientation of coronal planes (solid line) is parallel to the platform represented by a dashed line (see the white arrow). FIG. 5 shows a coronal TSE T2-weighted image of the mouse embedded in the OCT compound. FIG. 6 shows a histological section that corresponds to the coronal TSE T2-weighted image. FIG. 7 shows the histological section with hematoxylin and eosin staining, which also corresponds to the coronal TSE T2-weighted image. It is noted that the TSE T2-weighted image (FIG. 5) matches the histological sections (FIGS. 6 and 7).

ADC Map Reconstructed from DW Images with Various b Values

Figure 8:
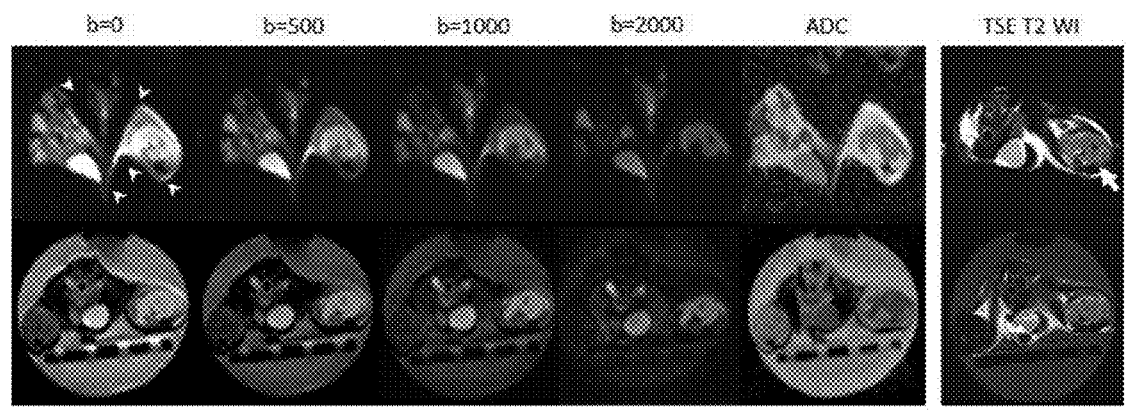
FIG. 8 shows DW images of the mouse before (upper row) and after (lower row) the OCT compound embedding.

The DW images of the mouse with various b values are shown in FIG. 8. Generally, the signal to noise ratio reduces as the b value increases. The upper row shows the DW images of the mouse before embedding, and the lower row shows the DW images of the mouse after the OCT compound embedding. The anatomical TSE T2-weighted images of the mouse before and after the OCT compound embedding are also shown in FIG. 8.

It is noticeable that when the mouse was not embedded in the OCT compound, all the DW images with different b values were distorted. Consequently, the reconstructed ADC map was distorted. In contrast, the distortion artifacts were reduced when the mouse was embedded in the OCT compound, which resulted in a more consistent image compared with the anatomical TSE T2-weighted image.

Percentage of Overlay Between ADC Map and TSE T2-Weighted Image

Geometric distortion of the in vivo DW images was assessed using MATLAB 7.0 (The Mathworks, Natick, Mass., USA). The contour of the mouse in the ADC map was drawn and superimposed onto the corresponding TSE-T2W image, which was assumed to be the non-distorted image for reference's purpose. The extent of geometric distortion was quantified by calculating the percentage of overlap between the ADC map and the TSE-T2W image:

$$\text{Overlap percentage} = \frac{\sum v_{ADC} \cap v_{TSE}}{\sum v_{ADC} \cup v_{TSE}} \times 100\%$$

where $v_{ADC}$ and $v_{TSE}$ represent the volumes of the target tissue extracted from the ADC map and the TSE-T2W image, respectively. The numerator and the denominator denote the number of voxels where the ADC map and the TSE-T2W image intersect (∩) and are in union (∪), respectively.

Figure 9:
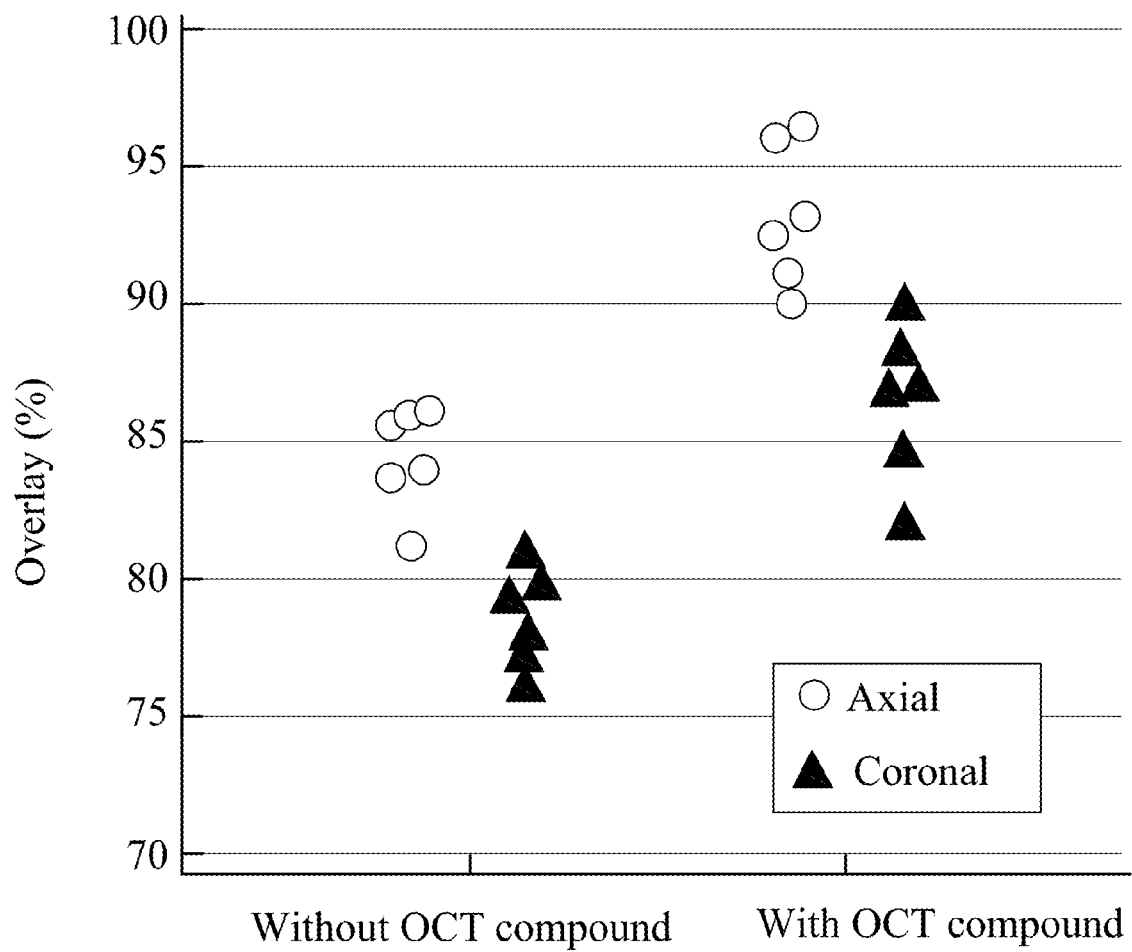
FIG. 9 shows a comparison of the percentage of overlay between DW images (ADC maps) and TSE T2 weighted images of the mice, before and after the OCT compound embedding.

FIG. 9 shows the overlay percentages for the DW imaging when the mice were embedded in the OCT compound compared with when the mice were not embedded. The geometric distortion of the in vivo DW imaging was significantly reduced after embedding in the OCT compound. The overlay percentage for the OCT compound-embedded mouse (axial: 93.3±2.6%; coronal: 86.7±2.9%) was significantly higher than that for the mouse that was not embedded (axial: 84.5±1.9%; coronal: 74.2±3.1%) in both the axial and coronal planes.

Visual Correlation

Figure 10:
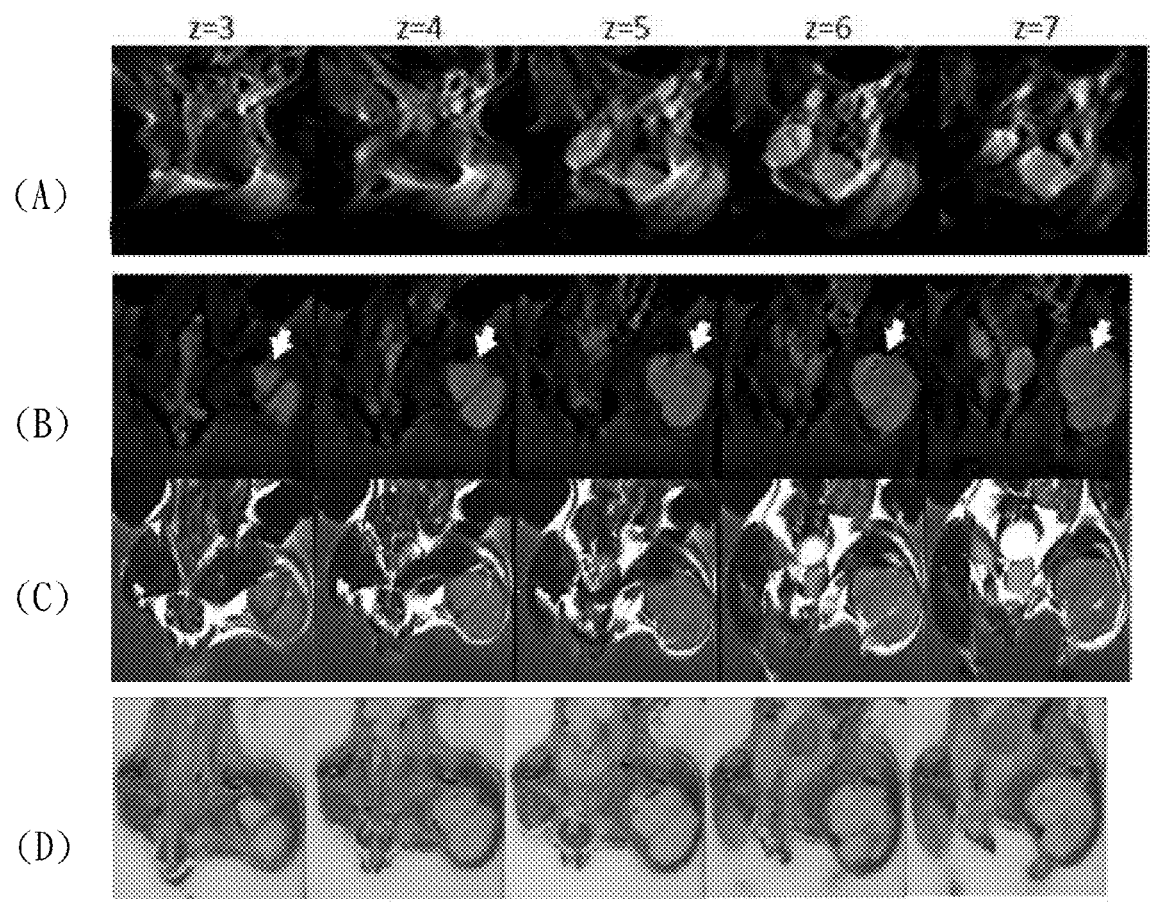
FIG. 10 shows MR images of the mouse and the depth-matched tissue sections.

FIG. 10 shows MR images of one of the mice and the depth-matched tissue sections: (A) DW images (b=1000 sec/mm$^2$) of the mouse in the coronal planes without OCT compound embedding, (B) DW images (b=1000 sec/mm$^2$) of the mouse in the coronal planes with OCT compound embedding, (C) anatomical TSE T2W images in the corresponding slice locations, and (D) histological sections matched to the depth of the corresponding MR images. The Z number represents the acquired slice number of the DW images. The white arrows indicate the location of the tumor.

The DW images after OCT compound embedding were visually correlated with histological sections in a slice-to-slice fashion. The DW images were distorted prominently when the mouse was not embedded in the OCT compound. The distortion in the DW images was reduced when the mouse was embedded in the OCT compound. The tumor was well visualized and appeared hyperintense in the DW images with a clear boundary, the morphology of which corresponded well to that in the TSE T2W images. The tissue sections cut directly parallel to the MR imaging planes were consistent with the in vivo DW and T2W images at each slice depth.

In sum, the OCT compound may serve as a medium to homogenize the magnetic field in MRI and support the package specimen for frozen section simultaneously. Animal and phantom experiments showed that the OCT compound produces a uniform $B_0$ field distribution around the imaging subject, allowing the acquisition of DW images with reduced distortion artifacts. The structure of the histological sections (sectioned slices) of the target tissue appears to be consistent with the in vivo MR images (DW images) in a slice-to-slice fashion. The method of this invention allows for direct correlation of the MRI results with the histological sections without complicated manipulation of specimens.

While the present invention has been described in connection with what is considered the most practical embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for correlating magnetic resonance images with histological sections, comprising the steps of:
    (a) embedding a target tissue of a living animal in an enclosed matrix of an optimal cutting temperature compound to obtain a packaged specimen which is disposed on a platform such that the packaged specimen is oriented in a first guiding plane;
    (b) subjecting the packaged specimen on the platform to an MRI examination by scanning the packaged specimen along imaging planes oriented parallel to the first guiding plane, thereby obtaining magnetic resonance images of the packaged specimen;
    (c1) transferring the packaged specimen to a cryostat; and (d) subjecting the packaged specimen in the cryostat to a frozen sectioning procedure along sectioning planes in parallel with a second guiding plane which is parallel to the first guiding plane to thereby obtain histological sections each of which is readily correlatable with a corresponding one of the magnetic resonance images.

2. The method according to claim 1, wherein, in step (a), the enclosed matrix is disposed in an enclosed space defined between a container and the platform, which is disposed in the container and which is removable from the container along an in-plane direction, a flat surface of the platform extending in the in-plane direction and defining both the first and second guiding planes.

3. The method according to claim 2, before step (d), further comprising a step (c2) of removing the platform together with the packaged specimen disposed thereon from the container.

4. The method according to claim 3, wherein, in step (a), a lower half of the living animal is fixed to the flat surface of the platform.

5. The method according to claim 1, wherein, in step (b), the packaged specimen is subjected to a diffusion MRI examination to obtain diffusion weighted images.

* * * * *